US00PP11108P

United States Patent [19]

Andersen et al.

[11] Patent Number: Plant 11,108

[45] Date of Patent: Oct. 26, 1999

[54] SOUR CHERRY CULTIVAR NAMED 'SUREFIRE'

[75] Inventors: Robert L. Andersen; Susan K. Brown, both of Geneva; Roger D. Way, Stanley; Kenneth G. Livermore, Geneva; David E. Terry, Ovid, all of N.Y.

[73] Assignee: Cornell Research Foundation, Inc., Ithaca, N.Y.

[21] Appl. No.: 08/885,762

[22] Filed: Jun. 30, 1997

Related U.S. Application Data

[63] Continuation of application No. 08/623,940, Mar. 29, 1996, abandoned, which is a continuation of application No. 08/366,421, Dec. 29, 1994, abandoned, which is a continuation of application No. 08/147,704, Nov. 4, 1993, abandoned.

[51] Int. Cl.[6] ..... A01H 5/00

[52] U.S. Cl. ..... Plt./181

[58] Field of Search ..... Plt./37, 181, 182, Plt./183

*Primary Examiner*—Howard J. Locker

[57] ABSTRACT

A new distinctive cultivar of sour cherry (*Prunus cersus*) which is exceptional in combining 1) high quality, totally red fruit, 2) a tree habit that has fewer lateral and secondary lateral branches than many other cultivars and which facilitates ease of hand harvesting, and 3) having a unique late season anthesis of its flowers so that they evade spring frost damage. The cultivar is named 'Surefire' and was tested as NY 12716.

6 Drawing Sheets

CROSS-REFERENCE TO RELATED APPLICATIONS

This application is a continuation of plant Application Ser. No. 08/623,940, filed Mar. 29, 1996, now abandoned, which is a continuation of plant Application Ser. No. 08/366,421, filed Dec. 29, 1994, now abandoned, which is a continuation of plant Application Ser. No. 08/147,704, filed Nov. 04, 1993, now abandoned.

BACKGROUND OF THE INVENTION

In 1975 hybrid seeds were created from controlled pollinations between 'Borchert Black Sour'×NY 6935 ('Richmorency'×'Schattenmorelle'). A population of seedlings with the New York State Agricultural Experiment Station breeding record designation 75323 were planted in 1976 in an orchard designated as Crittenden 30. One seedling in this population was planted in Row 1, Tree 136, and in 1981 it fruited for the first time and in 1982 it was selected for further testing because of its excellent yield on a young tree and its interesting intermediate red colored fruit (skin, pulp, and juice). It was designated NY 12716 and grafted in 1982 to 'Mazzard Seedling' rootstocks utilizing the nursery t-budding grafting technique. These grafts produced trees to be used for more tests of this selection's merit. Grafted trees that resulted were planted in 1984 in a Station field designated as Crittenden 29Row2Tree44 (Cr29R2T44). In 1984 further grafted trees resulted from using Cr29R2T44 buds for propagating wood and planting trees grafted to 'Mazzard Seedling' rootstocks in a Station orchard designated as Lucey 50 Row 1 Tree 10, T11, T12, T13, T14, T15. Subsequently fourth clonal generation trees were created utilizing buds for propagating wood taken from the L50R1T11. Such fourth generation trees were distributed to collaborators in the USA who assisted us in evaluating the merit of this selection under restricted nondistribution test agreements.

NY 12716 is being named and released as 'Surefire' and is the subject of this invention.

In all test plantings, trees of NY 12716 (now being named and released as 'Surefire') bore consistently good fruit crops as judged by experienced researchers and cherry orchardists. Some of these trees were tested during blossom time for pollenizer effectiveness on their own stigmas to determine if the selection had the self fruitful characteristic, which it did.

There follows comparison of traits of this selection as compared to the 'Montmorency' cultivar that is the primary commercial source cherry cultivar in the USA, comprising over 98% of all sour cherry orchards.

DESCRIPTION OF RELATED ART

We also refer here to Danish scientific literature cited to describe the differences in 95 sour cherry cultivars, namely, Christiansen, J. V., 1990, "A review of an evaluation of 95 cultivars of sour cherry," Danish Research Service for Plant Science Report No. 2043.

DESCRIPTION OF THE INVENTION

This invention relates to a new and distinctive cultivar of the sour cherry tree, 'Surefire', which we discovered in a test planting belonging to the New York State Agricultural Experiment Station, Cornell University, Geneva, Ontario County, N.Y. This discovery is a product of a cherry breeding research program of the New York State Agricultural Experiment Station. Experience since 1990 indicates the tree is a regular and consistent producer.

Pollination: We have conducted experiments to determine the pollination biology specifics about 'Surefire'. Our experiments took the form of field tests to cover the emerging flowers with paper bags and thereby isolate flowers of 'Surefire' from bee visitation. Such bagging allowed us to observe the effects of wind or other mechanical means of moving 'Surefire's' own pollen to the stigmas of 'Surefire' flowers within such bags. In all cases fruit with mature seeds were produced without cross pollination from sources other than 'Surefire's' own flowers. Hence we conclude that 'Surefire' is self fruitful and can be planted as individual trees which will not require a pollenizer cultivar to be interplanted with them to be fruitful.

Detailed plant description: Accompanying FIGS. 1–6 depicts leaves, fruits, and pits as well as the intact tree. The numerical color specifications employed in this patent disclosure are those of The Royal Horticultural Society Color Chart (1976):

Flowers and flowering: Flowers are borne on lateral branches or spurs on branches that are two years old or older. They also are borne from axillary buds or shoots laid down the previous growing season. Typically, 2 to 4 flowers are produced from spur buds and 2 to 4 flowers are also borne on axillary buds on the previous season's shoots. Flowers are normally borne in clusters that range from two to four blossoms per flower bud and the flower buds occur on both spurs and annual growth from the previous season where it is less than 12 to 14 inches in length; there is a much stronger tendency for 'Surefire' flowers to form in pairs than in the case of other commercial varieties. Such flowers emerge in Geneva about 4 to 7 days later than on the 'Montmorency' cultivar. In 1998, the full bloom stage in Geneva, N.Y., occurred for 'Surefire' on May 6, 1998, and for 'Montmorency' on May 2, 1998. From this date and by logical references from the Danish Scientific Literature referred to above, we conclude that 'Surefire' is one of the latest blooming sour cherry cultivars. Bloom period in Geneva, N.Y., for 'Surefire' is about five days in length. 'Surefire' tends to have a similar length of bloom period to the 'Meteor' cultivar which, like 'Surefire', has more spurs flowering and less production on annular growth than does the standard 'Montmorency' cultivar which blooms over a shorter period (two fewer days in Geneva, N.Y.).

Figure 1:
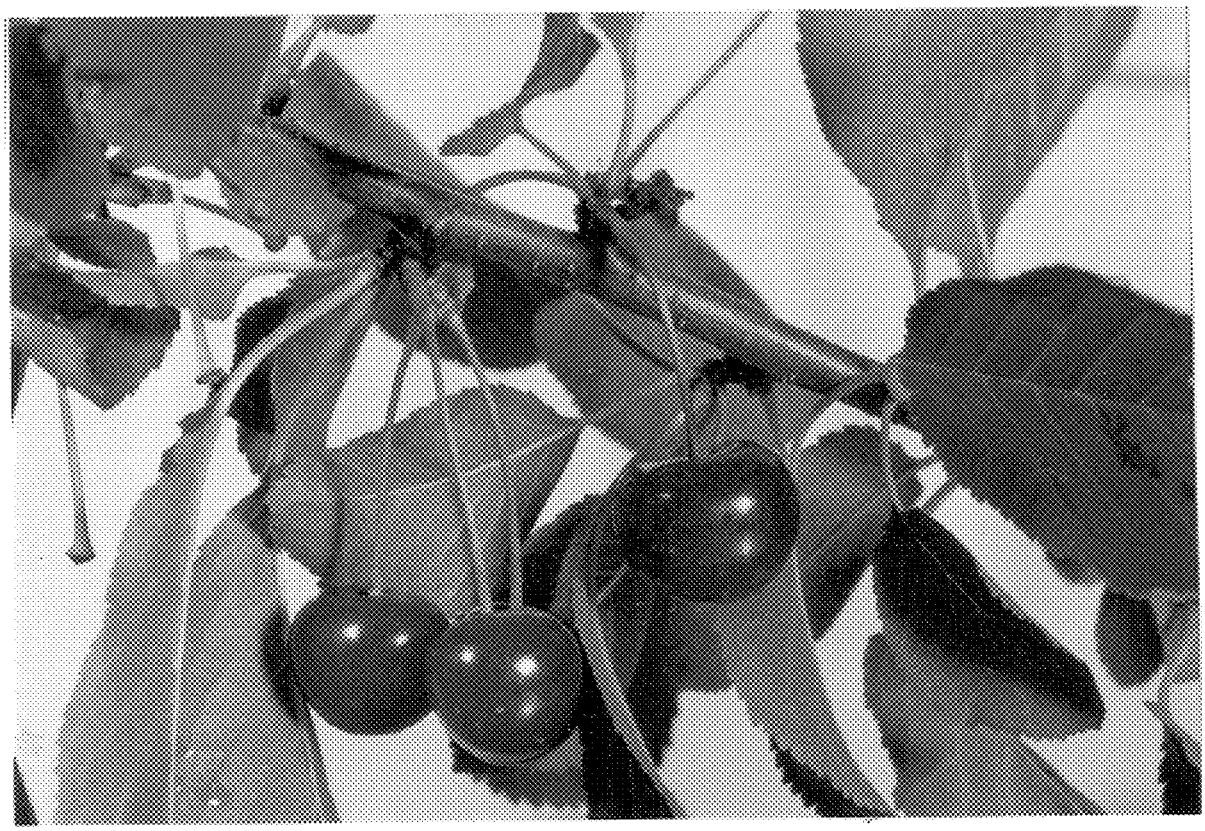
FIG. 1. Fruit of 'Surefire' growing on the tree
Figure 2:
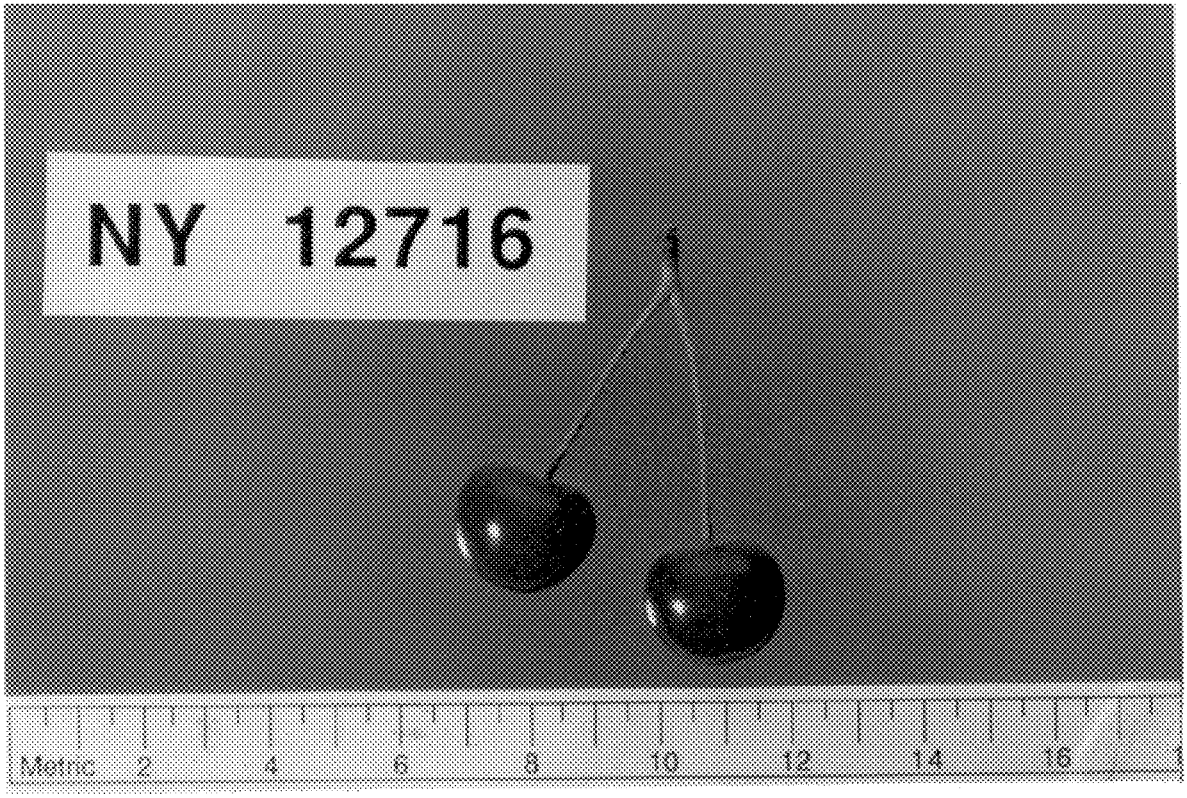
FIG. 2. Fruit of 'Surefire'

Flowers are white, single and have no unusual features that distinguish them from those of other sour cherry cultivars except that they open later than most other cultivars. They are structurally typical of *Prunus cerasus* with a base number of five petals and about 25 stamens. Pedicils are about 3.5 cm to 4.0 cm long and of intermediate thickness, about 1 mm. Pedicils are often forked with 2 round glands at the locus of the biforkation point and a small bract-like leaflet is usually also found attached in the same general region as the glands. Pedicel color from FIGS. 1 and 2 is yellow-green 148B. No maturity or seasonal differences in pedicel color changes from other commercially grown sour cherry cultivars have been noted. Anthers are yellow and pollen is yellow-orange.

Figure 3:
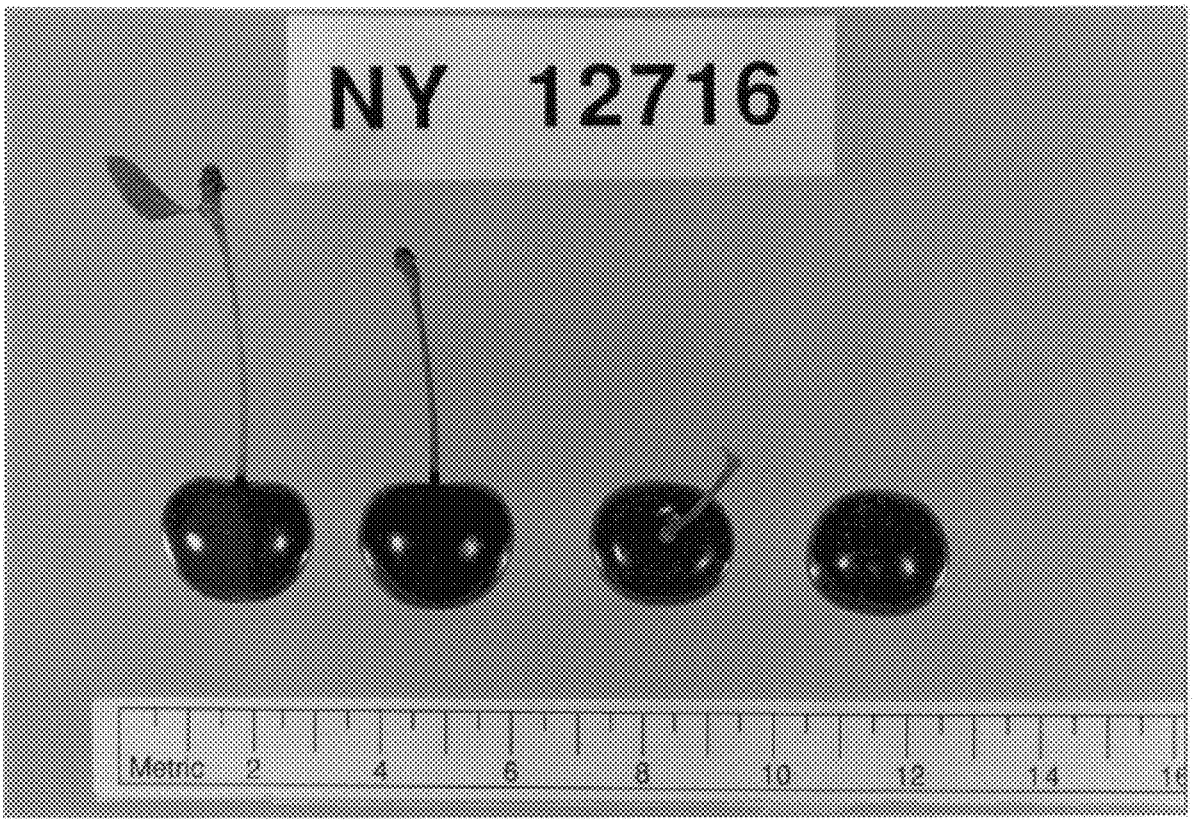
FIG. 3. Fruit of 'Surefire'
Figure 4:
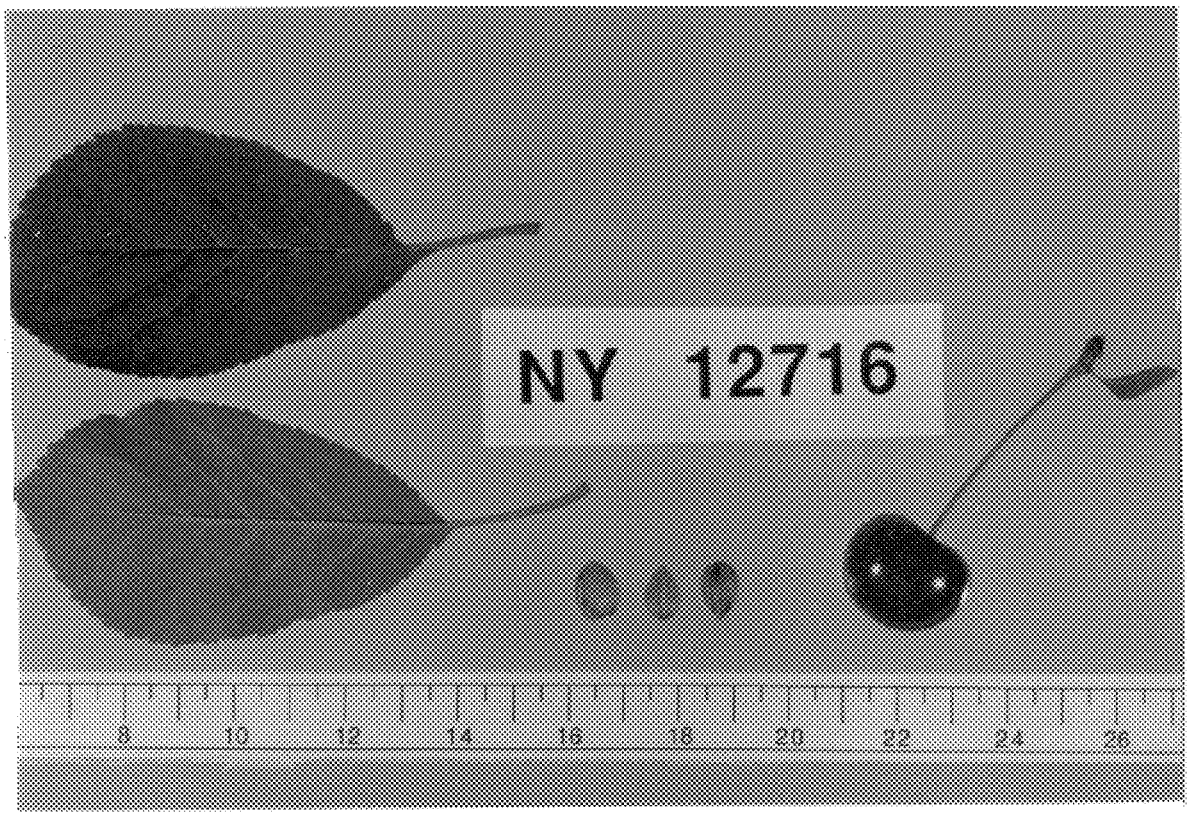
FIG. 4. Leaves, pits and fruit of 'Surefire'
Figure 5:
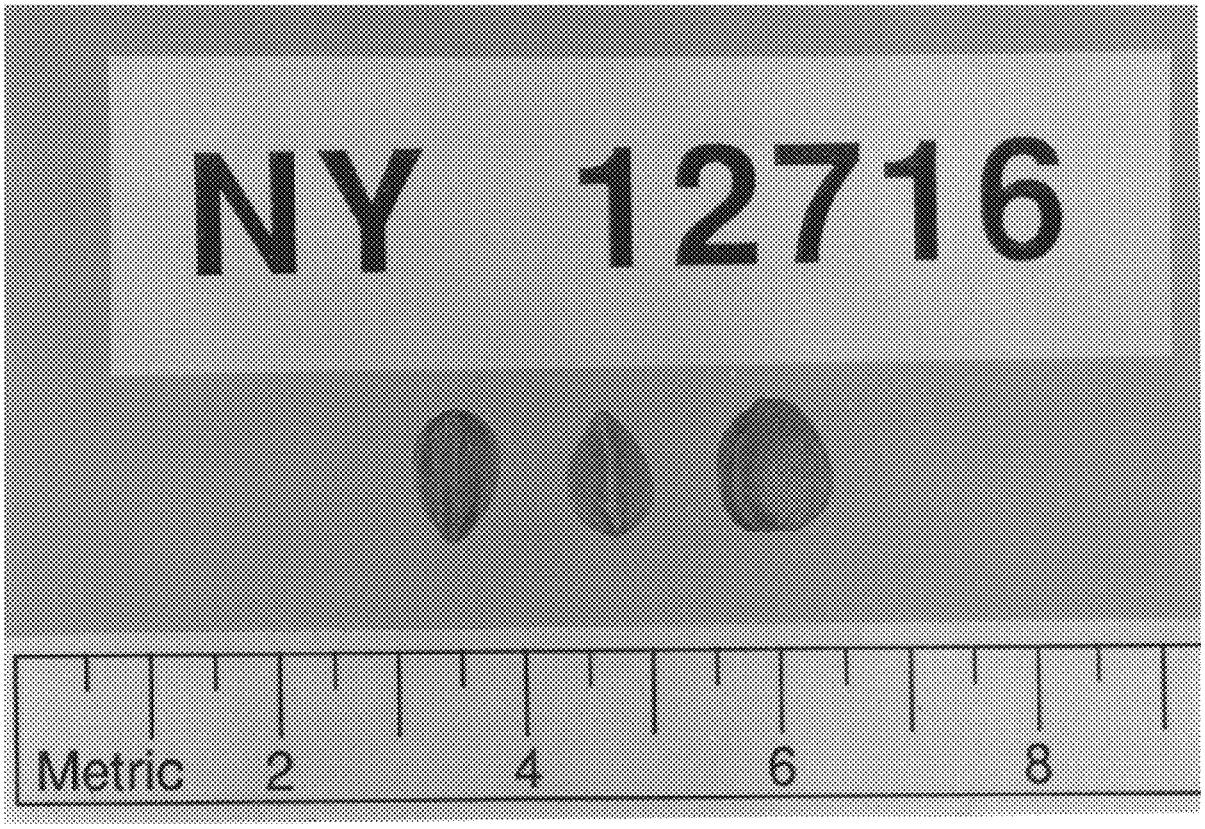
FIG. 5. Pits of 'Surefire' fruit
Figure 6:
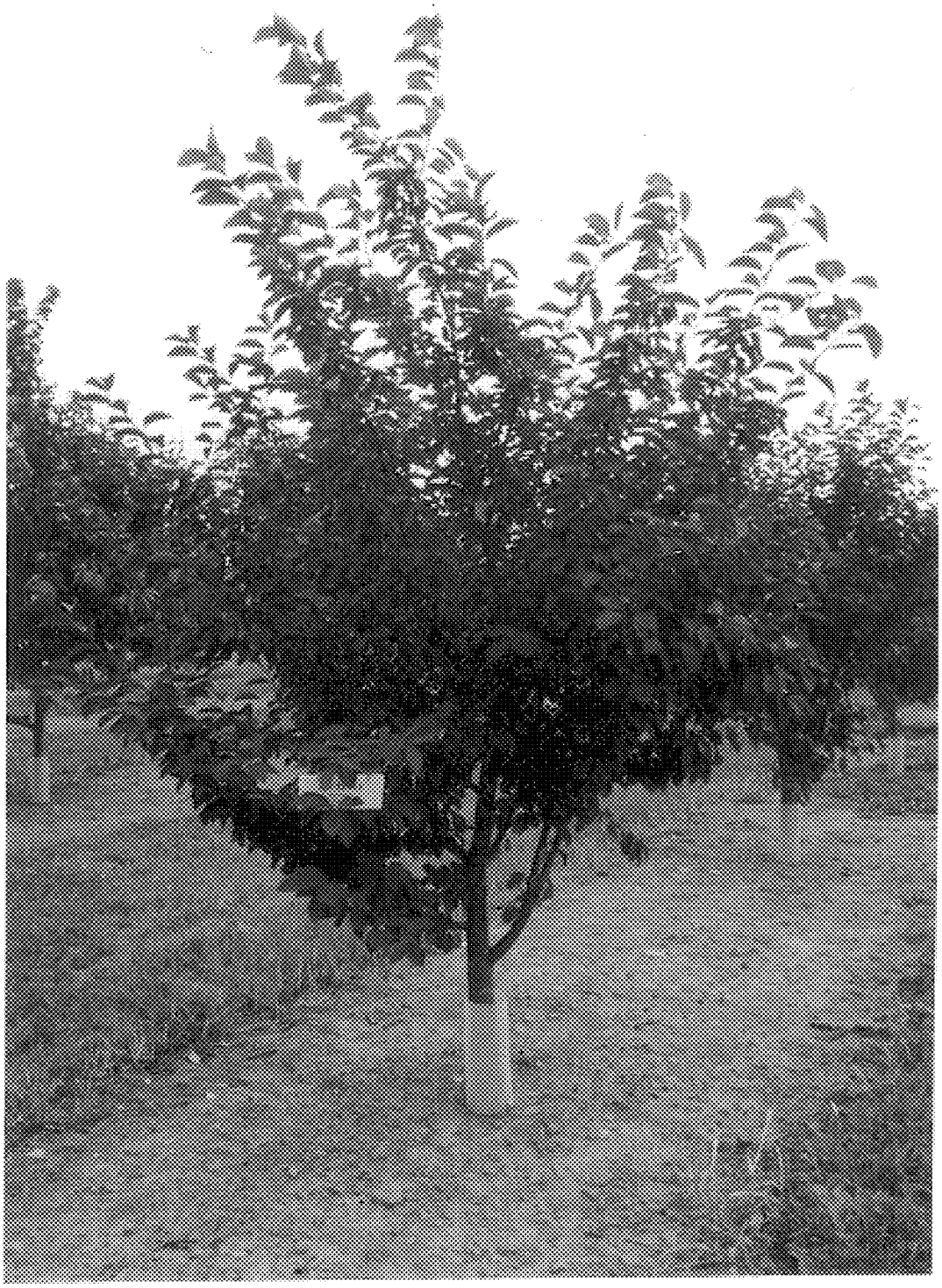
FIG. 6. 'Surefire' tree.

Fruiting habit and fruit: 'Surefire' trees (FIG. 6) which are grafted to the common cherry rootstock, Mazzard, typically have flowers produced after three growing seasons on tress that have been planted in their orchard position. Fruit is often set on trees which flower for the first time. The individual fruits of 'Surefire' (FIGS. 1 thru 3) are slightly cordate (heart shaped), their skin color at maturity is red group 53A whereas the 'Montmorency' skin color is red group 48B. Their flesh color is the same color as the skin. Juice color is pink but is officially categorized as red group 55B. Fruits are very symmetrical, and medium large size compared to most other sour cherry cultivars. They are about 2.2 to 2.6 cm in diameter or width and 2.0 cm long. Pit shape (FIG. 5) is oblong-conic with size being medium about 1.1 cm long and 0.9 cm wide across the suture and 0.8 cm wide in their flatter dimension with slightly protruding suture ridges and a very slight tip on the stigmatic end. Pits of 'Surefire' (FIGS. 4 and 5) are usually about 7.2% of the total fruit weight whereas 'Montmorency's' pit is slightly smaller, averaging about 6.2% of total fruit weight. By contrast 'Schattenmorelle,' the most prominent commercial cultivar in western European sour cherry producing regions, has a pit size that averages 7.9% of the total fruit weight. Pit color from FIG. 5 is greyed-orange 165D. Typical fruit is shown in FIG. 3. Fruits of 'Surefire' resist moisture stress induced cracking very well. The soluble solids level of 'Surefire' fruit is generally above 13 percent at maturity in Geneva. The nature acidity level of juice of 'Surefire' fruits has a pH of 3.1 compared to 3.3 for 'Montmorency' and titratable acidity of 1.6% for 'Surefire' and 1.3% for 'Montmorency'. The flavor of 'Surefire' fruits is strongly cherry-like and the good balance of natural sugars and natural acidity makes the quality of its fruit particularly appealing. Their flesh is firmer than many other sour cherry cultivars. They have a fruit removal force at maturity of about 300 grams of pull force. For commercial shake-and-catch harvesting, growth regulators are applied a few days prior to harvest, to "loosen" the fruit from the pedicels to reduce the fruit removal force so it does not exceed 250 grams of pull force at harvest time as is the case for all sour and sweet cherries that are grown for commercial shake-and-catch harvesting in the Great Lakes Region. Fruit ripening is about 65 days after full bloom in Geneva. In 1998, harvest occurred for 'Surefire' in Geneva, N.Y. on July 22 and for 'Montmorency' on July 12. Thinning of crops has not been necessary to attain greater size and is not contemplated. It is believed that the cultural practice of applying plant growth regulators would be beneficial to the culture of 'Surefire' after it has cropped regularly for six to eight years.

Tree habit: 'Surefire's' tree habit (FIG. 6) is medium in vigor, upright in form due to strong apical dominance in the central leader with many fewer lateral scaffold branches than the 'Montmorency' cultivar. Scaffold branches are also less prone to produce secondary lateral branches than 'Montmorency' and this characteristic produces a tree that is much more open to the sun's penetration to the interior of the tree than trees of many other sour cherry cultivars. This is a distinctive feature of this cultivar with many lateral spurs produced along all portions of the previous season's growth.This tree habit and branching structure leads to a natural pyramid form to the tree crown in mature, unpruned fruiting trees. 'Surefire' requires substantially less care in training and pruning than does the standard sour cherry cultivar 'Montmorency' because it has wider angles to its lateral branches and fewer of them. As the tree of 'Surefire' matures to full capacity for cropping, it needs fewer total pruning cuts because it has much less biforkation of its limbs and hence less brushy wood to remove to achieve good light penetration that is essential for flower bud initiation and spur retention.

Shoots: 'Surefire's' shoots are of medium length with few lateral branches. They have small, numerous rectangular lenticels arranged perpendicular to the stems main axis. In the autumn after cessation of terminal growth, the color of the bark at the fourth internode above the proximal position is mottled and mostly grey group 201B with patches of greyed-orange 175B interspersed. This pattern of mottling reverses to mostly greyed-orange 175B with small patches of grey group 201B in the center and apical regions of longer shoots. Bark of 'Montmorency' shoots is greyed-orange 177A throughout.

Leaves: Leaves of 'Surefire' (FIG. 4) are medium in leaf area, usually symmetrical, lamella glabrous and smooth with adaxial lamella surface yellow-green 147B, abaxial surface yellow-green 148C. Whereas, by contrast 'Montmorency's' similar leaf surfaces are yellow-reen 146A and 147C. Margins are rounded serrate with 5 to 5.5 serrations per cm and major serrations are often notched near their center point. Whereas, by constrast 'Montmorency' serrations are usually smaller, about 0.4 cm, and much less deeply notched. Glands are seldom present on the petiole but two small round glands are usually present at the basal fringe of the leaf blades. Color of petioles from FIG. 1 is yellow-green 148B. No maturity or seasonal differences in foliage color changes from other commercially grown sour cherry cultivars have been noted.

Tree size: The oldest trees observed are at Geneva, N.Y. and are about 14 feet tall on Mazzard rootstock and have topped-out due to heavy cropping. They are about 2 feet shorter than neighboring trees of 'Montomorency' in the same orchard row. Neighoring trees of 'Meteor' and 'English Morello' planted at the same time in the same year are less than 10 feet tall. It is assumed that use of mahaleb rootstocks or other, even more dwarfing stocks, would cause proportionally less vigor and growth, and the trees of each of the cultivars mentioned would be proportionally smaller.

Planting systems: The tree of 'Surefire' crops readily and regularly by its third year after planting and does not require trellising to encourage earlier flower bud initiation and earlier cropping. The tree is suitable for high density orchard systems so long as the orchardist understands the spacings that their harvesting and other implements will require. 'Surefire' requires about 10 to 15 percent less space per tree than 'Montmorency' due to different tree habit and earlier and more regular cropping tendencies.

Resistance to common diseases and pests: 'Surefire' like all other commercial source cherry cultivars is not resistant to cherry fruit fly. 'Surefire' is slightly more susceptible to European red mite and two spotted mite than is 'Montmorency' and therefore requires more careful monitoring and consideration of insecticidal control strategies that help integrated pest management (IPM) strategies reduce possibilities of economic losses due to mite "bronzing" (losses in photosynthetic capacity to support the regular heavy crops of 'Surefire'). 'Surefire' is similar to other commercial sour cherry cultivars in requiring pesticide or mating disruption IPM strategies to control lesser peach tree borer, plum borer, and common peach tree borer since mechanical shake-and-catch harvesters cause some damage to trunks to mature sour cherry trees of all commercial cultivars. 'Surefire', like other sour cherry cultivars, is more genetically tolerant to black cherry aphids than are sweet cherries but, like other sour cherry cultivars, requires IPM strategies. 'Surefire' is more tolerant to common brown rot caused by *Monilinia fruticola* (which is a pest of all stone fruits grown in the USA), presumably because the blossom blight phase of the disease is less likely to occur due to better weather during bloom due to later bloom time which, on average in New York, is less likely to be rainy, which favors brown rot control. European brown rot which is caused by *Monilinia laxa*, and which is less common in New York and Great Lakes Region cherry orchards than common brown rot, is more likely to cause a serious disease loss in 'Surefire' than in 'Montmorency', which is known to be highly tolerant to this disease. Bacterial canker, which is known to cause disease in 'Montmorency' in cool wet springs and at sites that favor retention of early morning dew and fog, causes less damage to 'Surefire'. Cherry leaf spot fungal attacks which require careful development of IPM strategies for all sour cherry orcharding in the Great Lake Regions, has similar levels of tolerance in 'Surefire' and 'Montmorency'. More arid states where sour cherries are produced, like Utah and eastern Washington, will have markedly less fungal pest attacks on 'Surefire' as well as on the 'Montmorency' cultivar.

Usefulness

'Surefire' sour cherry is well suited for production to fulfill certain commercial orchardist's needs for a high quality, self fruitful sour cherry that will evade spring frost damage to flowers and provide them with consistent crops of cherries for U-pick market operations. The open habit of the 'Surefire' tree is also well suited to hand picking that is used in such operations. Home gardeners will also appreciate this cultivar because of the same features that appeal to U-pick operations.

What is claimed is:

1. A new and distinct sour cherry cultivar as herein described and illustrated.

* * * * *